United States Patent [19]

Quackenbush

[11] Patent Number: 5,104,388

[45] Date of Patent: Apr. 14, 1992

[54] MEMBRANE SPLITTABLE TUBING

[75] Inventor: John J. Quackenbush, Hoover, Ala.

[73] Assignee: FBK International Corporation, Birmingham, Ala.

[21] Appl. No.: 521,131

[22] Filed: May 8, 1990

[51] Int. Cl.⁵ ............................................... A61M 5/00
[52] U.S. Cl. ..................................... 604/264; 604/164
[58] Field of Search ............... 604/160, 164, 264, 280; 138/128, 156

[56] References Cited

U.S. PATENT DOCUMENTS

| | | | |
|---|---|---|---|
| 3,677,243 | 7/1972 | Nerz | 604/161 |
| 4,449,973 | 5/1984 | Luther | 604/272 |
| 4,451,256 | 5/1984 | Weikl et al. | 604/164 |
| 4,581,390 | 4/1986 | Flynn | 604/280 |
| 4,776,846 | 10/1988 | Wells | 604/280 |
| 4,865,593 | 9/1989 | Ogawa et al. | 604/160 |
| 4,874,374 | 10/1989 | Kousai et al. | 604/164 |
| 4,994,047 | 2/1991 | Walker et al. | 604/280 |

Primary Examiner—John J. Wilson
Assistant Examiner—Frank A. LaViola
Attorney, Agent, or Firm—Herbert M. Shapiro

[57] ABSTRACT

A splittable tube, useful in medical applications as a cannula for insertion into the body, comprises an inner and an outer layer. The inner layer defines a central lumen for accepting catheters and probes. The inner layer also includes a longitudinal slot through its wall for defining a stress line in the outer layer. The outer layer is very thin, membrane-like, and tears along the longitudinal stress line when the cannula is pulled to the side of a catheter occupying the central lumen. The tube may be made of electrically insulating material and used, for example, as strippable insulation as telephone or house wire, and strippable without the use of tools.

11 Claims, 2 Drawing Sheets

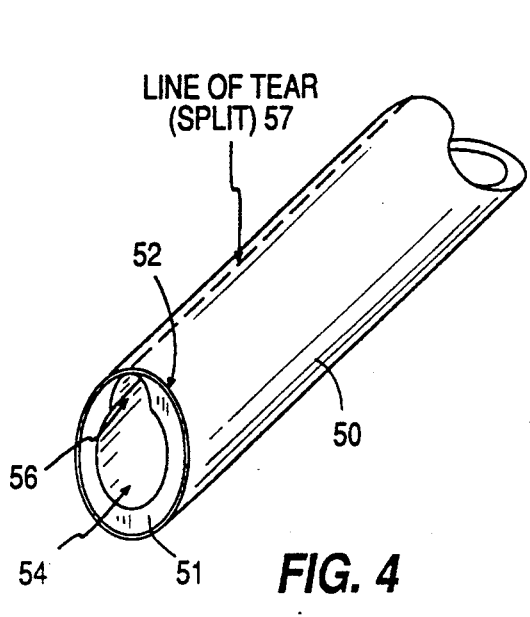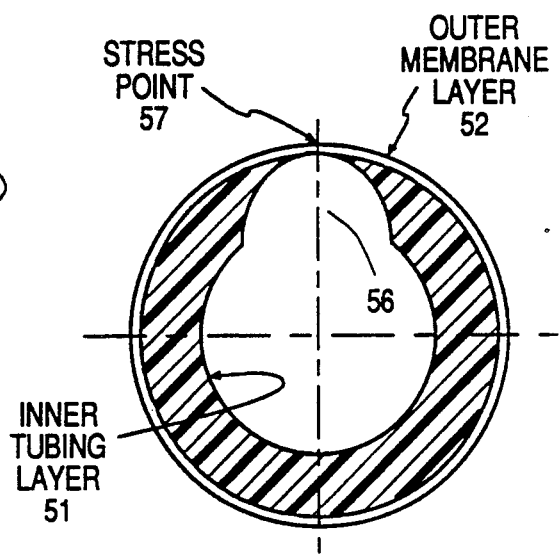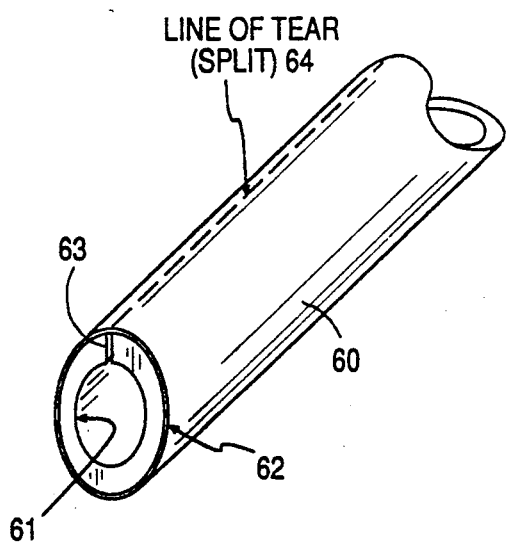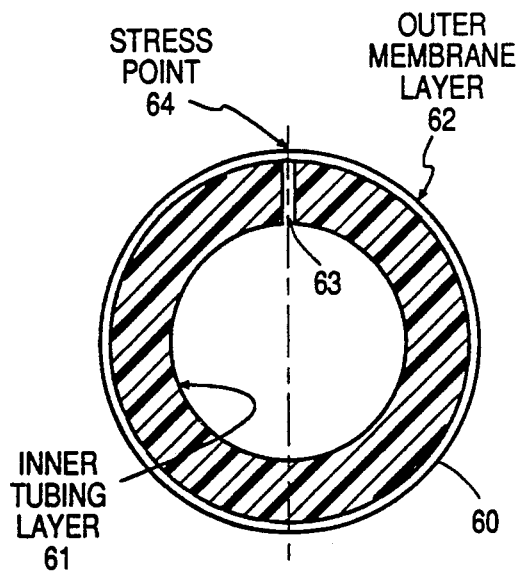

MEMBRANE SPLITTABLE TUBING

FIELD OF THE INVENTION

This invention relates to "peel-away" tubing which may be used for electrical wire insulation and, more particularly, for medical usage such as a "peel-away" cardiovascular access port for sheaths and dilators.

BACKGROUND OF THE INVENTION

Catheters are frequently inserted into the human body by means of an aid called a "cannula." A cannula is a flexible tube which serves as a passageway into a blood vessel for a probe or catheter. When a probe or catheter is to remain in the body for an extended period, it is desirable to remove the cannula. However, removal of the cannula is not always a simple task. Frequently, a probe or catheter has an enlarged proximal end which makes the removal of the cannula (sleeve) difficult. This problem has been alleviated by a cannula which separates into two parts as described, for example, in U.S. Pat. No. Re. 13,855 issued Mar. 26, 1985 and in U.S. Pat. No. 4,166,469 issued Sept. 4, 1979. Although the apparatus described expedites removal of the cannula, it requires two hands to remove it, requires a tab at the proximal end of each side of the cannula, requires a sleeve within a sleeve, and requires a line of apertures or particular molecular properties, to ensure that the cannula tears along a longitudinal direction.

BRIEF DESCRIPTION OF ILLUSTRATIVE EMBODIMENTS OF THIS INVENTION

In accordance with the principles of this invention, a peel-away sleeve for use as electrical wire insulation or for a cannula for medical usage includes an inner and outer sleeve. The outer sleeve is a thin membrane. The inner sleeve has a center opening into which, for example, a catheter is inserted. The inner sleeve also includes an off-center side bore in the wall of the inner layer, extending all the way through the wall of the inner layer.

The cannula is peeled away merely by pulling the cannula to one side of the catheter, so that the catheter enters the side bore separating the wall of the inner layer of the cannula and tearing the membrane outer layer Removal can be accomplished by grasping the proximal end of the cannula between two fingers of a hand and pulling to one side. The proximal end of the cannula includes a marking to designate the direction in which the proximal end should be pulled.

BRIEF DESCRIPTION OF THE DRAWING

FIGS. 3, 4 and 6 are plan views of alternative embodiments in accordance with the principles of this invention.

FIGS. 5 and 7 are cross-sectional views of the embodiments of FIGS. 4 and 6 respectively.

DETAILED DESCRIPTION OF ILLUSTRATIVE EMBODIMENTS OF THIS INVENTION

Figure 1:
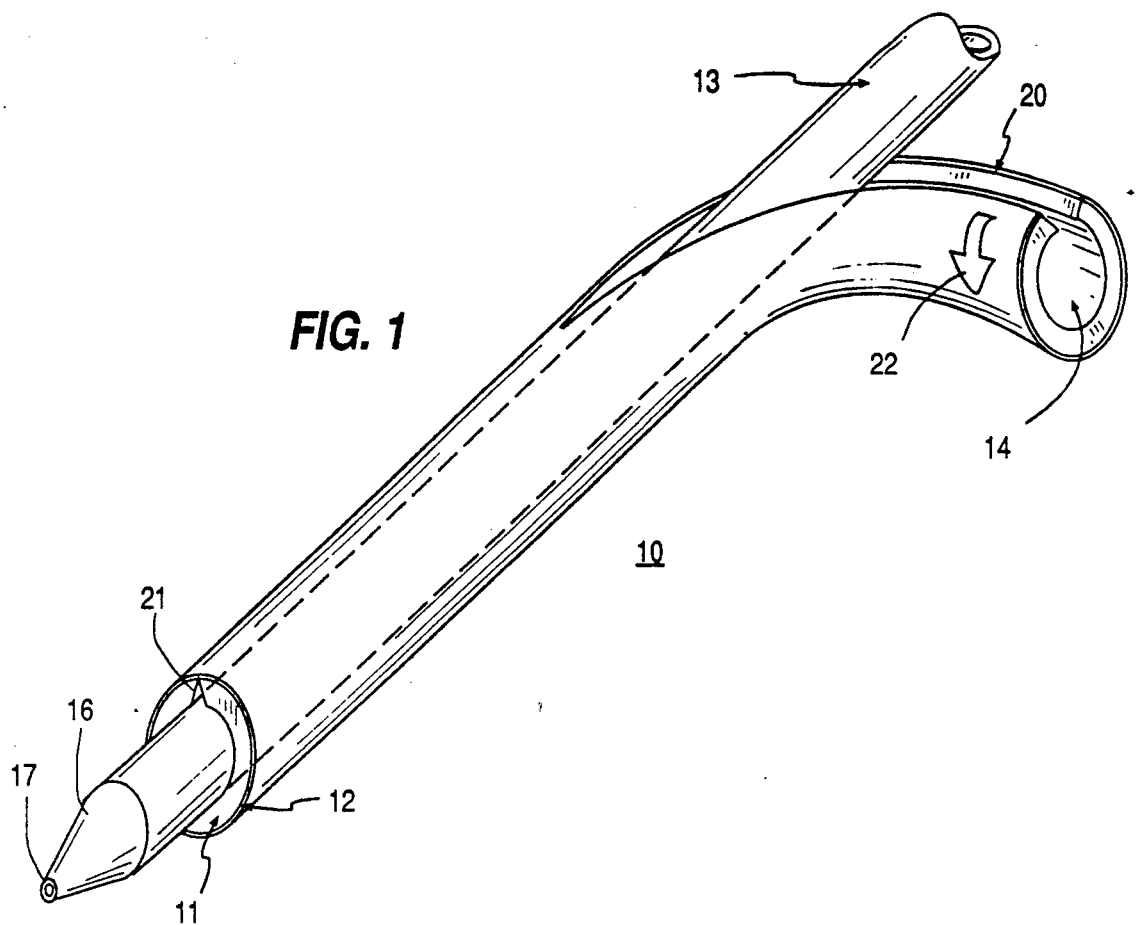
FIG. 1 is a schematic plan view of a peel-away tube in accordance with the principle of this invention with an inserted rod, wire, catheter, dilator or other central rod or tube in place.

FIG. 1 depicts a peel-away tube 10 comprising an inner layer 11 and a relatively thin outer layer 12. The figures also show a catheter 13 inserted within the central bore 14 of the tube. Only a portion of the catheter is shown. The proximal end of the catheter protruding from the partially peeled away tube is shown broken away The distal end 16 is shown extruding from the tube and, itself, including a central lumen 17.

In medical use, the tube is a cannula inserted into the human body frequently with the aid of a dilator. The dilator is used to extend a puncture wound in the body. The cannula is disposed about the dilator and enters the wound through the extended opening. The dilator is then removed, leaving the central bore of the cannula to receive, for example, a catheter to measure the flow of saline solution through a blood vessel. Such a catheter has a balloon at its distal end to close off the flow through a blood vessel when inflated. The balloon is inflated by air pressure from a fitting at the proximal end; thus, the proximal end of the catheter has a saline supply fitting, an air supply fitting, and may include a sensor fitting.

The tube (cannula in this case) is removed from its position merely by grasping the proximal end 20 and by pulling the end in a direction opposite to the longitudinal opening 21 in the inner wall 11. Tube 10 includes a marking arrow 22 to indicate the direction in which to pull. The axial opening can be seen to be triangular or wedge-shaped in a cross-sectional view of the tube as shown in FIG. 1 when the tube is peeled away, moved into the wedge 21 and causes a longitudinal stress line along the tip of the wedge. This, in turn, causes the membrane-thin outer layer to tear, along the longitudinal line at the stress point.

Figure 2:
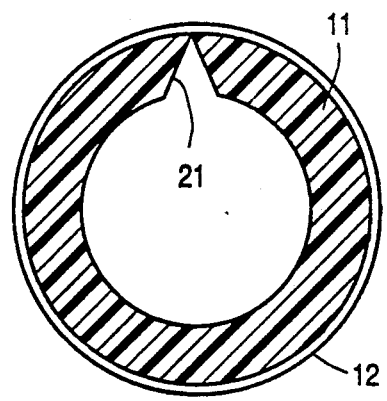
FIG. 2 is a cross-sectional view of the tube of FIG. 1.

FIG. 2 also shows typical dimensions for a cannula for medical use for accepting a probe or catheter. The inside diameter (ID) of the inner layer 11 is 0.060". The outside diameter (OD) of the inner layer is 0.998" and the outer layer is 0.001". These dimensions are only illustrative; the outer layer may be, for example, less than 0.001". The outer layer maintains the circumferential integrity of the tubing until the layer is split.

Figure 3:
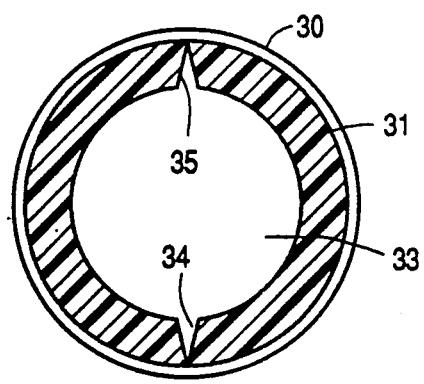

FIG. 3 shows a cross-section of an alternative peel-away tube. The tube again has an outer layer 30 and an inner layer 31; but in this case, the interior bore 33 has two longitudinal wedges 34, 35 penetrating the interior layer. The two wedges are 180° apart as can be seen from the figure and provide opposing stress points so that the cannula can be removed from either side. In the case where two stress points are provided, the direction marking may not be necessary because separation of the cannula into two parts is easily achieved by pulling in any direction.

Other geometries for the longitudinal cut in the inner wall are possible. FIGS. 4 and 5 show a splittable tube 50 having inner and outer walls 51, 52. The tube has a central lumen 54 and a longitudinal slot 56 in the inner wall. The longitudinal slot can be seen to have a circular or oval geometry defining a longitudinal stress line 57.

Similarly, FIGS. 6 and 7 depict a splittable tube 60 having an inner layer 61 and an outer layer 62. This embodiment includes a simple slot 63 through the wall of the inner layer. Slot 63 defines a stress line 64. It has been found that a catheter inserted into the central lumen of a splittable cannula in accordance with the principles of this invention causes the splitting to occur in the tube rather quickly if the longitudinal slot in the inner wall is of a shape to permit the catheter to enter and cause a spreading motion to the sides of the slot. However, this shape to the slot is not necesary. The shape of the longitudinal slot, the materials used and the thickness of the outer wall are considerations which may be traded off against one another.

The tubes of FIG. 1 can be made from any extrudable resin, but it is preferred, particularly for medical usage, that the inner layer be made of low-density (2.5 melt index, 0.925 specific gravity) polyethylene such as Dow 640.

The outer layer may be made from FDA-grade 0.933 density polypropylene with a melt flow rating between 7 and 9, such as Himont polypropylene T7673. Many polypropylenes are made up of long molecular chains which tend to line up in the longitudinal directions when extruded. Thus, polypropylene has a tendency to split along the direction of extrusion and in an uniformly straight line.

Many other materials may be extruded in combination, including:

a. Union Carbide high-density polyethylene (0.945 S.G.)
b. DuPont Surlyn ionomers (#1701)
c. Dow medical-grade polyurethane (2363 series)
d. B. F. Goodrich Estane polyurethane (type 5533)
e. Atochem nylon (e.g., BESNO 11)
f. USI Chemical ethylvinyl acetate (e.g., NA293)
g. Unichem polyvinyl chloride (e.g., 9011A-02)

In medical applications, such as an over-sheath for dilators for cannulas, materials are chosen for the inner and outer layers of the splittable tube which provides bio-compatibility, drug compatibility, meet FDA requirements for cytotoxicity, and have the most desirable physical properties for stiffness, surface smoothness and/or flexibility. For non-medical applications, a dual-layer insulation for electrical wire is provided which is strippable without tools.

Splittable tubes of the type disclosed herein can be made by conventional extrusion equipment. Such equipment produces a melt flow through a die having a geometry to define the central bore and longitudinal slot in the inner layer of the tube. A second melt flow is provided to encompass the so-shaped inner layer in conventional fashion. Tubes made in this fashion are cut to size One end of the tube may then be heated by any appropriate means, such as by a heat gun, and the end may be stretched to yield a tapered end The tip may be cut at a point where the inside diameter coresponds to the outside diameter of a dilator to be used with the cannula.

The cannula, when used for the insertion of a pacemaker, for example, is usually sterilized using ethylene oxide and packaged with a dilator in a hermetically sealed plastic bag.

What is claimed is:

1. A flexible splittable tube, said tube comprising an inner layer having a central bore and a relatively thick wall, said tube also including a second outer layer having a relatively thin wall, said wall of said inner layer having extending therethrough at least a first longitudinal slot for defining a longitudinal stress point along said outer layer, said at least first longitudinal stress point having an inward facing opening of a size to provide a stress on said outer layer when forced apart said outer layer being frangible and of a thickness to split upon the removal of said tube in the presence of an in-dwelling catheter occupying said central bore.

2. A splittable tube as set forth in claim 1 wherein said longitudinal slot is wedge-shaped in cross-section.

3. A splittable tube a set forth in claim 1 also including a second longitudinal slot, said second slot being positioned opposite said first slot.

4. A splittable tube as set forth in claim 3 wherein said first and second slots are wedge-shaped.

5. A splittable tube as set forth in claim 1 including proximal and distal ends, said tube at its proximal end including a direction of pull indication.

6. A splittable tube as set forth in claim 1 wherein said slot is semicircular in cross-section.

7. A splittable tube as set forth in claim 1 wherein said inner and outer layers comprise extrudable resins.

8. A splittable tube as set forth in claim 7 wherein said inner and outer layers comprise low-density polyethylene and polypropylene respectively.

9. A splittable tube as set forth in claim 8 wherein said outer layer comprises a polypropylene comprising a long molecular chain which tends to line up along the longitudinal direction when extruded.

10. A splittable tube as set forth in claim 7 wherein said inner layer comprises low-density polyethylene and said outer layer comprises FDA-grade polypropylene having a melt flow rating between 7 and 9.

11. A splittable tube as set forth in claim 1 wherein said inner and outer layers comprise electrically insulating material.

* * * * *